United States Patent [19]

Broudy et al.

[11] Patent Number: 4,854,566
[45] Date of Patent: Aug. 8, 1989

[54] ORTHOPEDIC DEVICE

[75] Inventors: Arnold S. Broudy, Pittsburgh; Cheryl A. Shank, Monroeville, both of Pa.

[73] Assignee: ABC Orthoproducts, Inc., Pittsburgh, Pa.

[21] Appl. No.: 144,236

[22] Filed: Jan. 15, 1988

[51] Int. Cl.$^4$ .............................................. B25B 1/20
[52] U.S. Cl. ...................................... 269/44; 330/154
[58] Field of Search ....................... 269/37, 40, 44, 104, 269/154, 156, 216, 322–325

[56] References Cited

FOREIGN PATENT DOCUMENTS 44140  3/1985  Japan .................................. 269/154

Primary Examiner—Gene Wan
Attorney, Agent, or Firm—Reed Smith Shaw & McClay

[57] ABSTRACT

The present invention pertains to an orthopedic device for immobilizing an appendage of a patient. The orthopedic device includes a linkage and a first member fixedly secured to the linkage. The first member has a side and an open region defined in the side. The orthopedic device also includes a second member which is slidingly secured to the linkage. The second member is capable of sliding along the linkage to be positioned adjacent the first member. The second member has a first side and a first open region defined in the first side. The first open region of the second member communicates with the open region of the first member when the second member is adjacent to the first member such that the first and second members are capable of being positioned about the appendage through the open regions of the first and second members.

8 Claims, 2 Drawing Sheets

ORTHOPEDIC DEVICE

FIELD OF THE INVENTION

The present invention relates to an orthopedic device. More specifically, the present invention relates to an orthopedic device for immobilizing an appendage of a patient.

BACKGROUND OF THE INVENTION

Currently, there is a need for a simple and quick device to immobilize an appendage of a patient in surgery or in an X-ray facility. In surgery, with many doctors, nurses and technicians of an operating team already in attendance, it is desirable to immobilize the appendage of a patient without the aid of someone in the operating team who possibly interferes with or is taken away from other tasks during an operation. In an X-ray facility, the hazards of exposure to X-rays dictate the need for a device to immobilize an appendage so an X-ray technician does not need to be in close proximity to the patient being X-rayed.

Several techniques have been developed to immobilize an appendage of a patient's body. A leg positioning device including a pair of adjustably spaced leg support means for X-ray examination of the leg is disclosed by U.S. Pat. No. 4,232,681. A device for clamping a human limb in a fixed position during X-ray examination, including a generally U-shaped clamp assembly is disclosed in U.S. Pat. No. 4,181,297. A device which varies the space between a series of pillows to accommodate a baby's head which is comprised of a pair of head cushions adjustably mounted via screws is described in U.S. Pat. No. 4,321,718. However, the problem with each of these immobilizing devices is that they do not afford a simple and quick procedure to immobilize an appendage and at the same time have the ability to adapt to the different sizes of the same appendages of different patients as well as to the different appendages themselves.

SUMMARY OF THE INVENTION

The present invention pertains to an orthopedic device for immobilizing an appendage of a patient. The orthopedic device is comprised of a linkage and a first member fixedly secured to the linkage. The first member has a side and an open region defined in the side. The orthopedic device is also comprised of a second member which is slidingly secured to the linkage. The second member is capable of sliding along the linkage to be positioned adjacent the first member. The second member has a first side and a first open region defined in the first side. The first open region of the second member communicates with the open region of the first member when the second member is adjacent to the first member such that the first and second members are capable of being positioned about the appendage through the open regions thereof.

In a preferred embodiment of the orthopedic device, the second member has a second side and a second open region defined in the second side, and the orthopedic device also includes a third member having a side and an open region in the side. The third member is fixedly attached to the linkage such that the second member is disposed between the first and the third member and the second member is capable of sliding along the linkage to be positioned adjacent to the third member. The open region of the third member communicates with the second open region of the second member when the third member is adjacent to the second member such that the second and third members are capable of being positioned about the appendage through the open region of the third member and the second open region of the second member.

The different open regions allow for immobilization of the same appendage in different positions or of different appendages. The second member is preferably also able to slide between the first and the third members to allow for variation in the size of the appendage being immobilized.

DETAILED DESCRIPTION OF THE INVENTION

Figure 1:
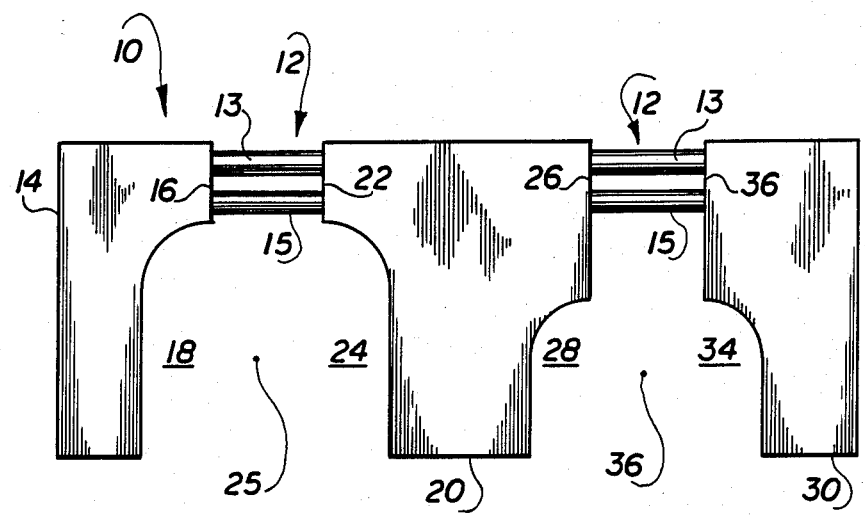
FIG. 1 is a side view of the orthopedic device.
Figure 2:
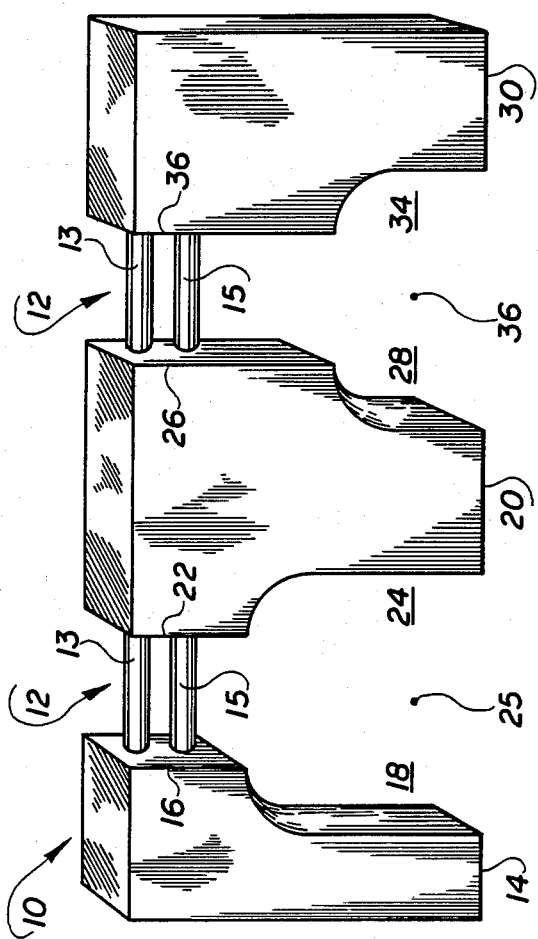
FIG. 2 is a top angular view of the orthopedic device of FIG. 1.

Referring now to the drawings, wherein like reference numerals designate identical or corresponding parts throughout the several views, and more particularly to FIG. 1 thereof, there is shown an orthopedic device 10 for immobilizing the appendage of a patient (not shown). The orthopedic device 10 is comprised of a linkage 12 and a first member 14 fixedly secured to the linkage 12. The first member 14 has a side 16 and an open region 18 defined in the side 16. The orthopedic device 10 is also comprised of a second member 20 which is slidingly secured to the linkage 12. The second member 20 is capable of sliding along the linkage 12 to be positioned in juxtaposition to, and preferably adjacent to, the first member 14. The second member 20 has a first side 22 and a first open region 24 defined in the first side 22. The first open region 24 of the second member 20 communicates with the open region 18 of the first member 14 when the second member 20 is adjacent to the first member 14 such that the first and second members 14, 20 are capable of being positioned about the appendage through and open region 18 of the first member 14 and the first open region 24 of the second member 20.

The linkage 12 may include a first rod 13 and preferably also a second rod 15 on which the first member 14 is fixedly secured and the second member 20 is slidingly secured. This attachment can be accomplished, for example, by placing holes in and through the first and second members 14, 20 so the rods 13, 15 can penetrate the first and second members. The ends of the rods 13, 15 in the first member are then secured in place by known attachment means, such as epoxy cement, to the first member 14. The ends of the rods 13, 15 that are positioned outside the second member 20 have, for example, a flanged area which is of a larger diameter than the holes through which the rods 13, 15 fit. The second member 20 is free to slide along the rods 13, 15 but cannot slide off the rods 13, 15 because the flanged ends stop it in one direction and the first member stops it in the other direction.

The first member 14 has a side 16 and an open region 18 defined in the side 16 that is approximately contoured to the shape of a portion of the appendage that it is to be positioned about. The second member which is slidingly secured to the linkage 12 has a first side 22 and a first open region 24 defined in the first side 22 that is also approximately contoured to the shape of the portion of the appendage it is to be positioned about. The open region 18 of the first member 14 and the first open region 24 of the second member 20 together form a third open region 25 when the first member 14 is adjacent to the second member 20. The third open region 25 is approximately contoured to support an appendage.

When the orthopedic device 10 is applied to immobilize an appendage, the first open region 18 of the first member 14 is positioned about a portion of the appendage to which it is approximately contoured, and the second member 20 is slid along the linkage 12 until it is essentially positioned about the position of the appendage to which it is approximately contoured. The first and second members 14, 20 are then adjacent to each other with the appendage therebetween through the open region 18 of the first member 14 and the first open region 24 of the second member 20. A support member (not shown) upon which the appendage and the orthopedic device 10 rests prevents the appendage from moving out of the orthopedic device.

The larger the appendage, the less member 20 will have to be slid along linkage 12 for the first member 14 and the second member 20 to be positioned about and immobilize the appendage. The smaller the appendage, the further second member 20 will have to slide for the first member 14 and the second member 20 to be positioned about and immobilize the appendage. The first and second members 14, 20 are made of a material that is heavy enough to prevent most movement of the appendage without strain by the patient. Preferably, the material of which first and second members 14, 20 is made is lead.

In a more preferred embodiment of the orthopedic device 10, the second member 20 has a second side 26 and a second open region 28 defined in the second side 26. There is also included in the orthopedic device 10 a third member 30 having a side 32 and an open region 34 defined in the side 32. The third member 30 is fixedly attached to the linkage 12 such that the second member 20 is disposed between the first member 14 and the third member 30. The attachment to the linkage 12, and rods 13, 15 specifically, for example is in a similar fashion to the way the first member 14 is fixedly attached to the rods 13, 15. In this embodiment, the flanged ends that prevent the second member 20 from sliding off the rods 13, 15 in the two member embodiment may be removed and the rods extended into the third member 30 where they are secured by known means, such as epoxy cement.

In the more preferred embodiment, the second member 20 is capable of sliding along the linkage 12 to be positioned adjacent to the third member 30 as well as the first member 14. The open region 34 of the third member 30 communicates with the second open region 28 of the second member 20 when the third member 30 is positioned adjacent to the second member 20 such that the second and third members 20, 30 are capable of being positioned about the appendage they are to immobilize through the open region 34 of the third member 30 and the second open region 28 of second member 20. The second open region 28 of second member 20 and the open region 34 of third member 30 together define a fourth open region 36 which is preferably of a different contour than the third open region 25 to permit the same appendage to be immobilized in a second position, or to permit a different appendage to be immobilized by the orthopedic device. The second and third members 20, 30 are applied in a similar manner to immobilize an appendage as the first and second members 14, 20 are applied to immobilize an appendage.

The contour of the openings of the first, second and third members should conform approximately to the type and nature of appendage that is to be immobilized. The open region 18 of the first member 14 and the first open region 24 of the second member 20 which form the third open region 25 are preferably contoured to immobilize a human appendage such as a hand or forearm, in a first position which is, for example, an anterior or posterior position. The open region 34 of the third member 30 and the second open region 28 of the second member 20 which form the fourth open region 36 are preferably contoured to immobilize a human appendage, such as a hand or forearm, in a second position which is, for example, a lateral position.

The orthopedic device 10 can be used to immobilize any appendage, or portion thereof, and is not limited to use with humans. It can also be used with animals.

Although the invention has been described in detail for the purposes of illustration, it is to be understood that such detail is solely for that purpose, and that variation can be made therein by those skilled in the art without departing from the spirit and scope of the invention except as it may be limited by the claims.

We claim:

1. An orthopedic device for immobilizing an appendage of a patient comprising:
   a linkage;
   a first member fixedly secured to the linkage, said first member having a side and an open region defined in the side; and
   a second member slidingly secured to the linkage, said second member capable of sliding along the linkage to be positioned adjacent to the first member, said second member having a first side and a first open region defined in the first side with said first open region communicating with the open region of the first member when the second member is adjacent to the first member such that the first and second members are capable of being positioned about the appendage through the open region of the first member and the first open region of the second member.

2. The device of claim 1 wherein said second member has a second side and a second open region defined in the second side;
   and further comprising a third member having a side and an open region in the side, said third member fixedly attached to the linkage such that the second member is disposed between the first and the third member and the second member is capable of sliding along the linkage to be positioned adjacent the third member, with the open region of the third member communicating with the second region of the second member when the third member is adjacent to the second member such that the second and third members are capable of being positioned about the appendage through the open region of the third member and the second open region of the second member.

3. An orthopedic device for immobilizing an appendage of the human body comprising:
   a linkage;
   a first member fixedly secured to the linkage, said first member having a side and an open region defined in the side;

a second member slidingly secured to the linkage capable of sliding along the linkage to be positioned adjacent to the first and third members, said second member having a first side and a first open region defined in the first side and a second side and a second open region defined in the second side; and A third member fixedly secured to the linkage such that the second member is disposed between the first and third members, said third member having a side and an open region defined in the side;

wherein the first open region of the second member communicates with the open region of the first member when the second member is adjacent to the first member such that the first and second members are capable of being positioned about the appendage through the open region of the first member and the first open region of the second member, and further wherein the second open region of the second member communicates with the open region of the third member when the third member is adjacent to the second member such that the second and third members are capable of being positioned about the appendage through the open region of the third member and the second open region of the second member.

4. The device of claim 3 wherein the linkage is a rod.

5. The device of claim 3 wherein the linkage includes two parallel rods.

6. The device of claim 3 wherein the first, second and third members are made of lead.

7. The device of claim 3 wherein the open region of the first member and the first open region of the second member together form a third open region when the first member is adjacent to the second member, said third open region approximately contoured to immobilize an appendage in a first position; and wherein the open region of the third member and the second open region of the second member together form a fourth open region when the third member is adjacent to the second member, said fourth open region approximately contoured to support an appendage in a second position.

8. An orthopedic device for immobilizing an appendage of the human body comprising:

a first rod and a parallel second rod adjacent to the first rod;

a first lead member fixedly secured to the first rod and the second rod, said first member having a side and an open region defined in the side;

a second lead member slidingly secured to the first and second rods with the first and second rods penetrating therethrough, said second member having a first side and a first open region defined in the first side, and a second side and a second open region defined in the second side;

a third lead member having a side and an open region defined in the side, said third member being fixedly secured to the first and second rods with the first and second rods penetrating therein such that the second member is disposed between the first and third members;

wherein said second member is capable of sliding along the first and second rods to be positioned adjacent to the first or third members such that the first open region of the second member communicates with the open region of the first member to form a third open region when the second member is adjacent to the first member, said third open region approximately contoured to immobilize the appendage in an anterior-posterior position;

and further wherein the second open region of the second member communicates with the open region of the third member to form a fourth open region when the third member is adjacent the second member, said fourth open region approximately contoured to support the appendage in a lateral position.

* * * * *